US012414762B2

(12) United States Patent
Huang et al.

(10) Patent No.: US 12,414,762 B2
(45) Date of Patent: Sep. 16, 2025

(54) SURGICAL DEVICE

(71) Applicant: ASTRON MEDTECH CORPORATION, Wilmington, DE (US)

(72) Inventors: Yi Hsi Huang, Taipei (TW); I-Lin Tsai, Taipei (TW); Kuei-Hua Chen, Taichung (TW)

(73) Assignee: ASTRON MEDTECH CORPORATION, Wilmington, DE (US)

( * ) Notice: Subject to any disclaimer, the term of this patent is extended or adjusted under 35 U.S.C. 154(b) by 272 days.

(21) Appl. No.: 18/343,513

(22) Filed: Jun. 28, 2023

(65) Prior Publication Data

US 2024/0050088 A1 Feb. 15, 2024

Related U.S. Application Data

(60) Provisional application No. 63/396,681, filed on Aug. 10, 2022.

(51) Int. Cl.
*A61B 17/04* (2006.01)
*A61B 8/00* (2006.01)

(52) U.S. Cl.
CPC ........ *A61B 17/0491* (2013.01); *A61B 8/4209* (2013.01)

(58) Field of Classification Search
CPC ............ A61B 17/0483; A61B 17/0469; A61B 17/06061; A61B 17/0491; A61B 17/0493; A61B 17/0485
See application file for complete search history.

(56) References Cited

U.S. PATENT DOCUMENTS 5,499,991 A * 3/1996 Garman ............. A61B 17/0483
606/148
2022/0240926 A1* 8/2022 Sauer ................ A61B 17/0482

* cited by examiner

*Primary Examiner* — Tuan V Nguyen
(74) *Attorney, Agent, or Firm* — Best & Flanagan LLP

(57) ABSTRACT

A surgical device has a housing having a hook portion at a distal end of the housing, an opening radially penetrating between the hook portion and the housing; a grasping structure comprising a rotating member rotatably positioned within the hook portion, having a notch radially recessed on a periphery of the rotating member, at least a portion of the notch corresponding to at least a portion of the opening; and reciprocating motion of an actuator along the axis for rotating the rotating member such that the open end of the notch is selectively connected to or misaligned with the open end of the opening.

12 Claims, 8 Drawing Sheets

SURGICAL DEVICE

FIELD OF THE INVENTION

The present invention relates to a surgical device.

BACKGROUND OF THE INVENTION

As modern medical technology becomes more advanced, minimally invasive surgery or small wound surgery has gradually become the goal in a surgical operation, which can not only achieve a quick and good wound healing effect, but also help the post-healing scar fade and improve. When a surgeon performs a suture in the body, the small operation space could not allow the surgeon to perform the operation deeper with hands, so the surgeon usually uses a long, thin surgical clamp or hemostatic forceps to facilitate the removal of the suture or the stitch in deep.

However, due to the dense and complex distribution of tissues in the body, and the fact that other surgical instruments will be placed in the body at the same time during surgery, if one is not cautious enough, the surgical clamp or hemostat could easily damage or pull the adjacent tissues and other surgical instruments when clamping the stitch or suture back and forth, causing unnecessary injuries. Therefore, the development of a product that allows the surgeon to easily perform stitching without damaging or pulling adjacent tissues and other surgical instruments is an urgent goal in the related industry.

SUMMARY OF THE INVENTION

In order to develop a product that facilitates a surgeon to perform stitching and avoids damaging or pulling the adjacent tissues and other surgical instruments, the present invention provides a surgical device comprising a housing having a receiving space inside, a hook portion extending downwardly and arcuately at distal end of the housing, an opening radially penetrating between the hook portion and the housing, a circle-like rotation space being formed inside the hook portion together with the opening, and the receiving space, the rotation space and the opening being connected to each other; a grasping structure positioned at a distal end of the housing, comprising a block-type rotating member having a similar circular shape rotatably placed in the rotation space, a notch radially recessed on a periphery of the rotating member, at least a portion of the notch corresponding to at least a portion of the opening; and an actuator, the reciprocating motion along the axial direction being used to rotate the rotating member so that the open end of the notch is selectively connected to or misaligned with the open end of the opening; and a driver used to drive the actuator in the reciprocating motion, wherein when the open end of the notch is misaligned with the open end of the opening, a connected receiving perforation is formed at the location of the notch and the opening corresponding to each other.

DESCRIPTION OF THE PREFERRED EMBODIMENTS

Figure 1A:
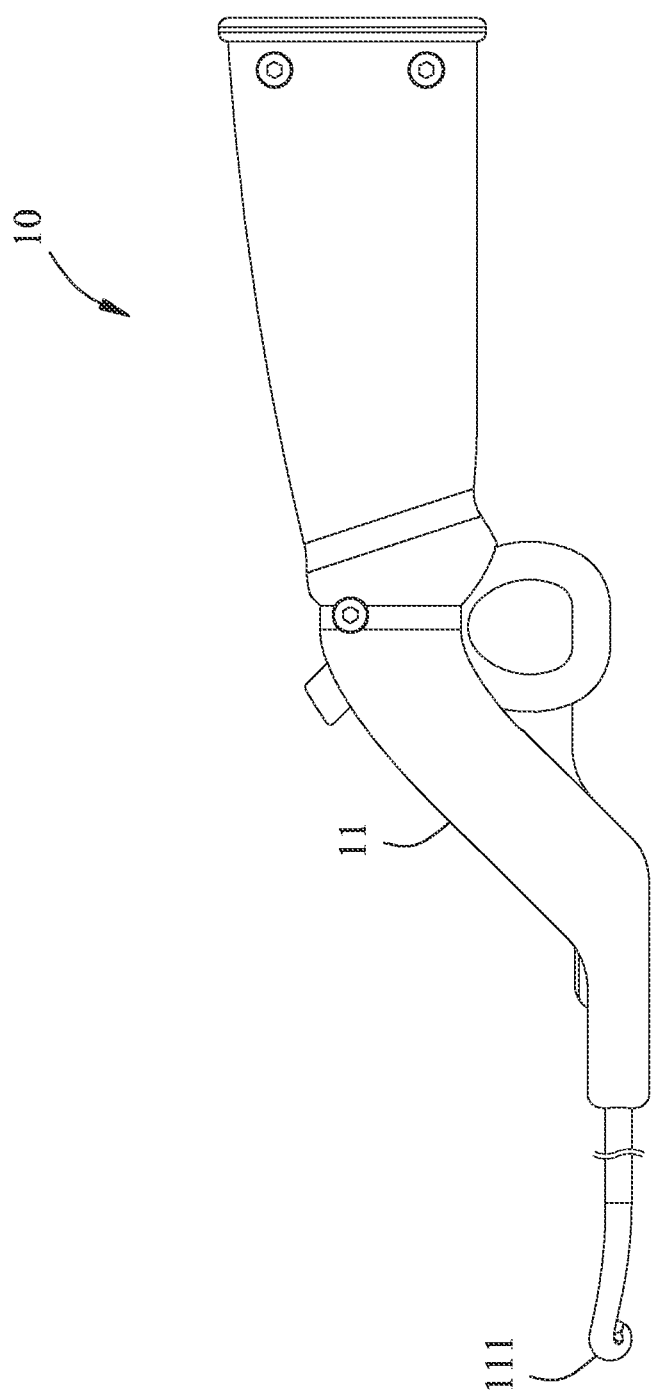
FIG. 1A is a side view of the preferred embodiment of the present invention.
Figure 1B:
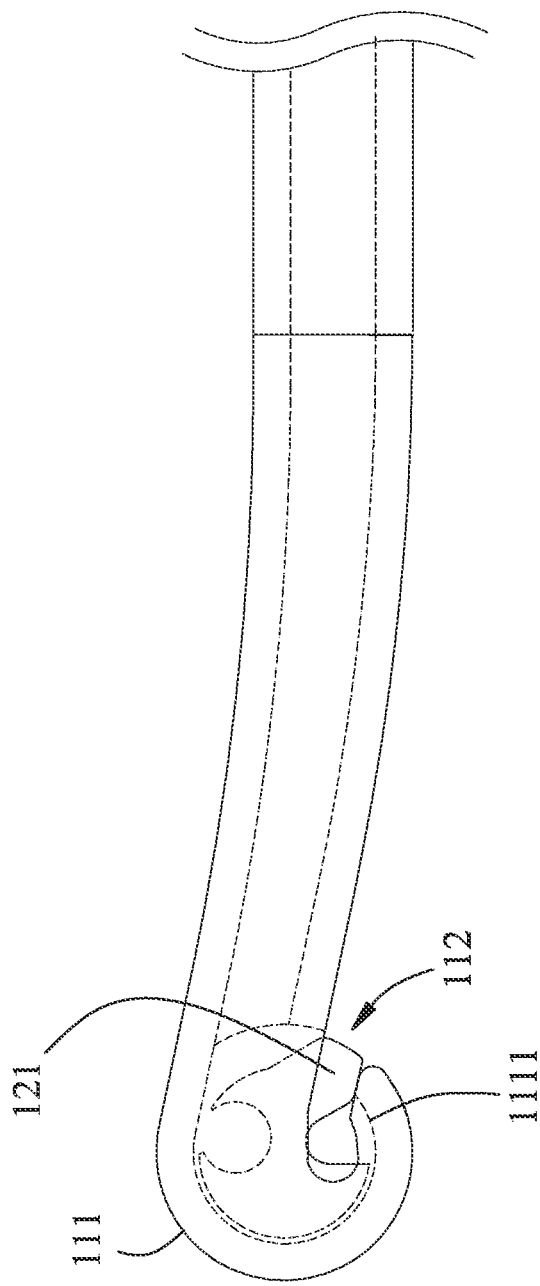
FIG. 1B is a partial enlarged view of the preferred embodiment of the present invention.
Figure 2A:
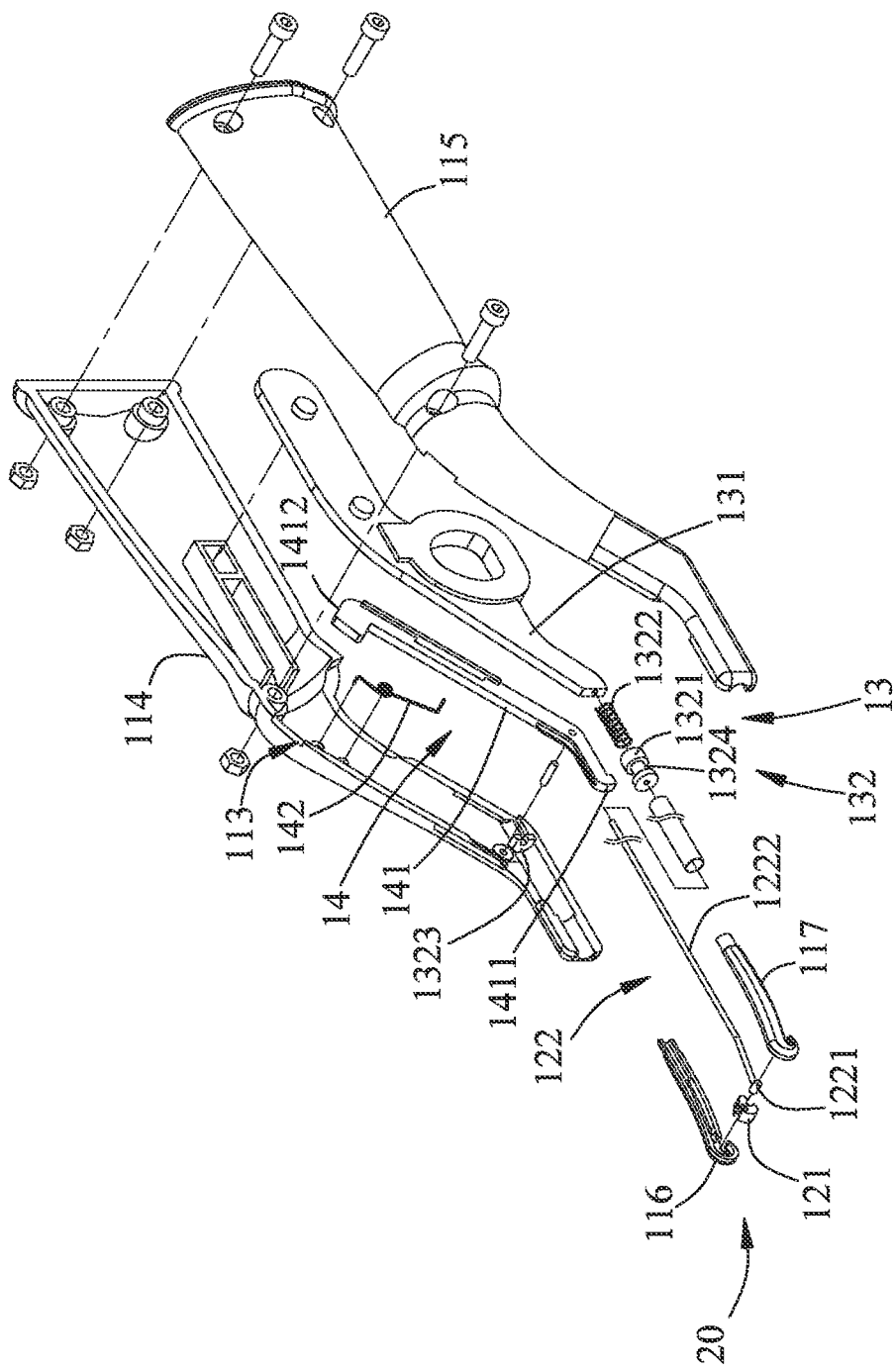
FIG. 2A is an exploded view of the preferred embodiment of the present invention.
Figure 2B:
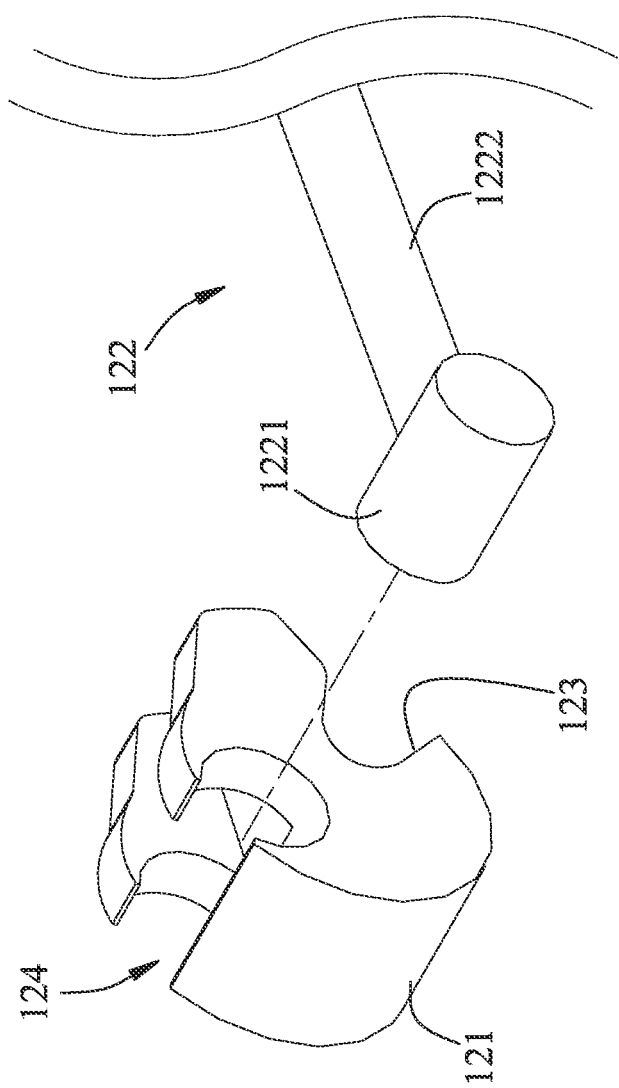
FIG. 2B is an enlarged view of the components of the preferred embodiment of the present invention.

Referring to FIGS. 1 and 2, a preferred embodiment of the surgical device 10 provided by the present invention comprises a housing 11 extending in an axial direction with a receiving space formed therein. A hook portion 111 extending downwardly and arcuately at a distal end of the housing 11, and the entire hook portion 111 is similar to a circular shape and the diameter of which is larger than the diameter of the housing 11 adjacent to the hook portion 111. An opening 112 radially penetrating between a hook end 1111 of the hook portion 111 and the housing 11. A circle-like rotation space is formed inside the hook portion 111 together with the opening 112, and the receiving space, the rotation space, and the opening 112 are connected to each other.

The housing 11 may consist of two components to be assembled up and down or left and right, but may also be assembled correspondingly with a number of components according to the requirement. In this embodiment, the housing 11 includes a left housing member 114 and a right housing member 115 at the proximal end, which can be assembled with each other, and the hook portion 111 at the distal end includes a hook left housing member 116 and a hook right housing member 117, which can be assembled with each other. wherein, when the hook left housing member 116 and the hook right housing member 117 are assembled, the diameter of the assembly is gradually reduced toward the distal end, and the proximal end of the assembly of the hook left housing member 116 and the hook right housing member 117 can be interconnected with the distal end of the assembly of the left housing member 114 and the right housing member 115. This helps the housing 11 to use the smaller outer diameter of the hook portion 111 (the left housing member 114 and the right housing member 115) to penetrate deeply into the surgical site to achieve a minimally invasive effect.

The housing 11 can be made to have a suitable appearance according to the practical application as desired, for example, the housing 11 can extend in a straight rod shape along the axis, or it can be in a curved shape with an angle. In this embodiment, the proximal end of the housing 11 extends horizontally toward the distal end, and the housing 11 extends downward at an angle relative to the horizontal at the middle portion and then returns to the horizontal extension adjacent to the hook portion 111 to form the distal end, wherein the angle is between 10 degrees and 60 degrees. In this way, the housing 11 can be made to conform to the shape of each part.

Figure 5:
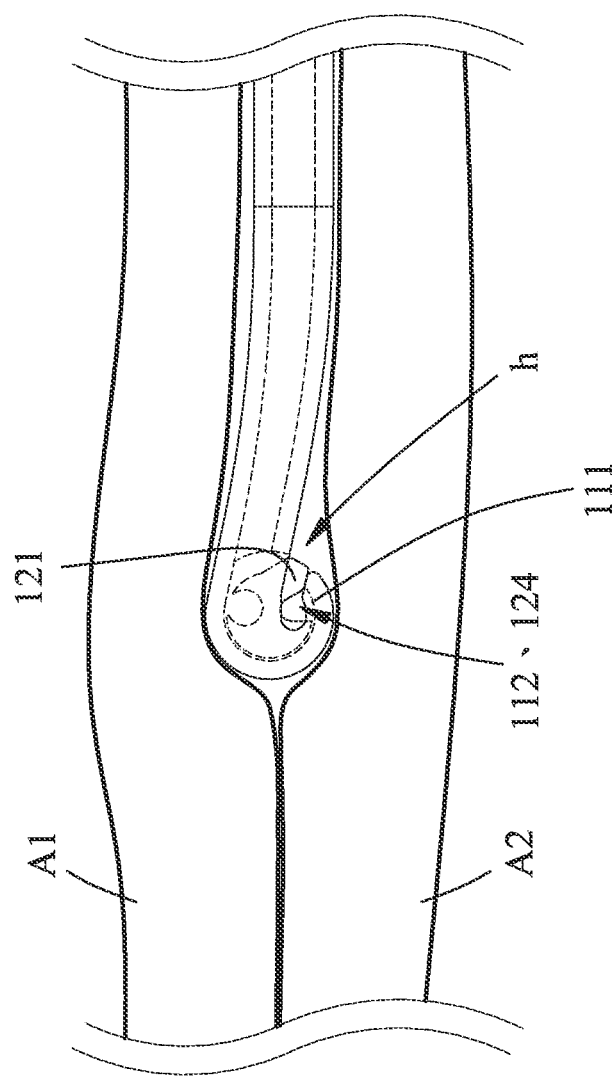
FIG. 5 is a schematic view of the use of the preferred embodiment of the present invention.

Further, with reference to FIG. 5, the housing 11 has a curved section 118 extending upwardly and arcuately adjacent to the hook portion 111, and the hook portion 111 is formed along the curved section 118 extending upwardly, so that the curved section 118 and the hook portion 111 as a whole have a curved upward appearance, and it is noteworthy that because the curved section 118 extends upwardly, a height difference space h is formed under the curved section and the housing 11 so that the hook end 1111 can be accommodated therein. This not only helps the hook portion 111 to penetrate deeper into the surgical site and move more smoothly between the two tissues A1, A2, but also prevents the hook end 1111 from hooking on the side of the tissue A2 when the hook portion 111 exits between the two tissues A1, A2.

In the housing 11, a gripping structure 12 is provided at the distal end and a driver 13 is provided at the proximal end, which is used to drive the gripping structure 12 to change its relative position. The gripping structure 12 includes a rotating member 121 and an actuator 122 arranged from the distal end to the proximal end, wherein the rotating member 121 is a circle-like block and can be placed in the rotation space by rotating in the direction of the axis.

The rotating member 121 is provided with a notch 123 recessed on a periphery in a radial direction, and when the rotating member 121 is positioned in the rotation space, at least a portion of the notch 123 corresponds to at least a portion of the opening 112. In this embodiment, the closed end of the notch 123 is connected to the closed end of the opening 112. The rotating member 121 can be rotated relative to the rotation space by the axial displacement of the actuator 122, so that the open end of the notch 123 can be selectively connected or misaligned with the open end of the opening 112. When the open end of the notch 123 is misaligned with the open end of the opening 112, a connected receiving perforation is formed at the location of the notch 123 and the opening 112 corresponding to each other.

Wherein, the manner of which the rotating member 121 is urged by the actuator 122 to rotate is not limited, as long as the rotation of the rotating member 121 can be associated with the axial displacement of the actuator 122 which should be covered within the scope of the present invention.

In this embodiment, the actuator 122 includes a rotating connector 1221 and a driving rod 1222. The rotating connector 1221 is a circular block and is connected to one end of the driving rod 1222 at any point on its periphery, the rotating member 121 has a rotating notch 124 recessed on the other periphery, and the rotating connector 1221 is rotatable in the rotating notch 124.

Figure 3:
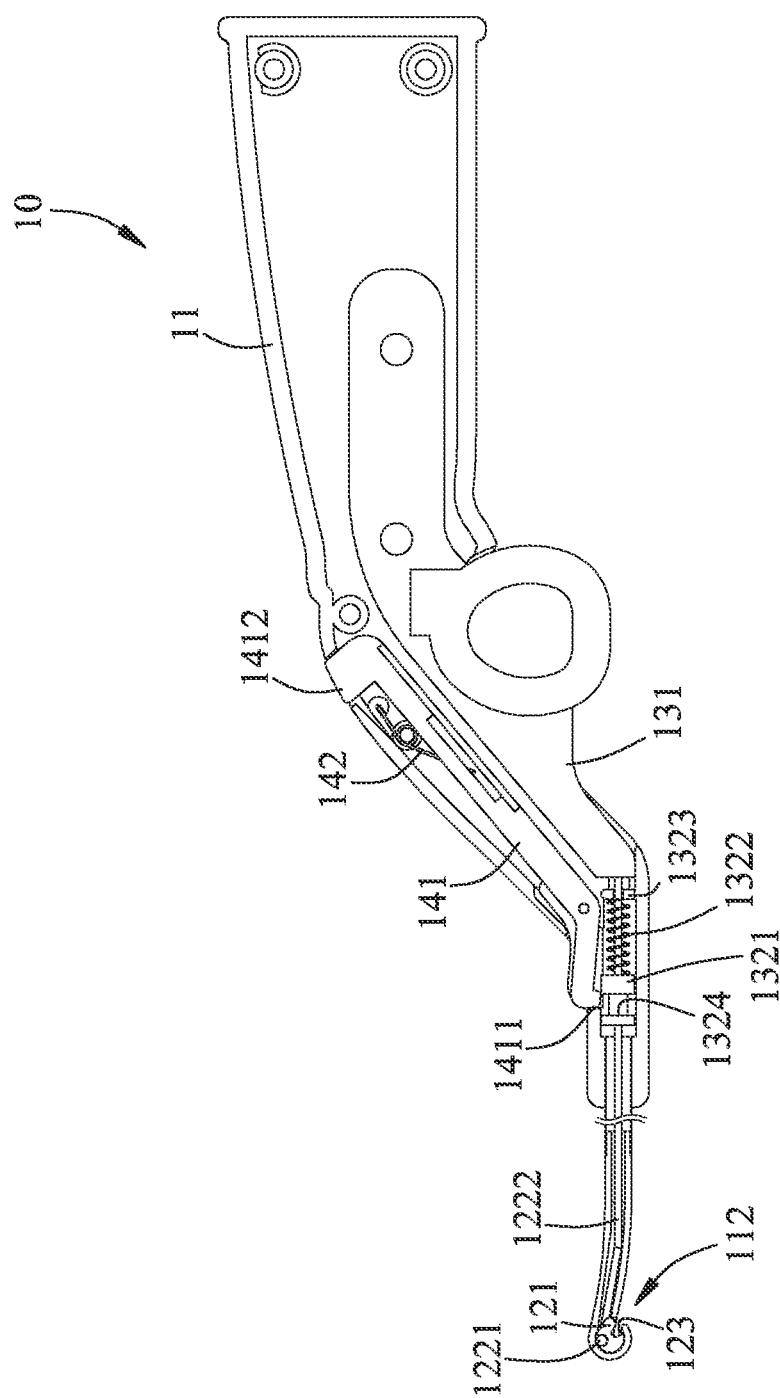
FIG. 3 is a schematic view of the first action of the preferred embodiment of the present invention.
Figure 4:
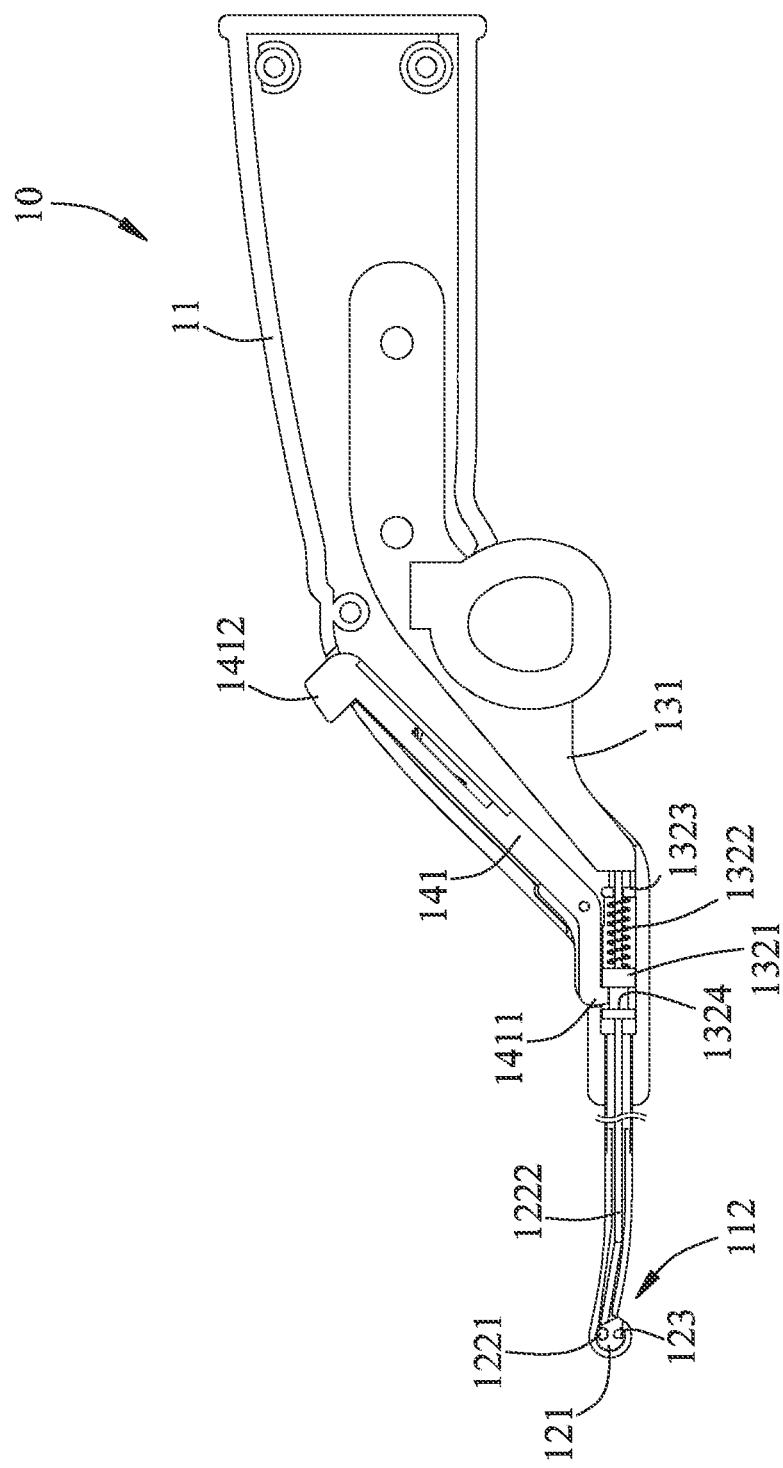
FIG. 4 is a schematic view of the second action of the preferred embodiment of the present invention.

With further reference to FIGS. 3 and 4, in the starting position shown in FIG. 3, the rotating member 121 is disposed in the rotation space, and the open end of the notch 123 is connected to the open end of the opening 112. The rotating connector 1221 is positioned where the rotation space is connected to the receiving space and near the top of the housing 11, and the driving rod 1222 extends toward the proximal end corresponding to the rotating connector 1221.

In a driving position shown in FIG. 4, the driving rod 1222 is displaced toward the proximal end, and at this time, the driving rod 1222 pulls the rotating member 121 through the rotating connector 1221 so that a push-pull force is generated over the rotating member 121 toward the proximal end, so that the rotating member 121 rotates relative to the rotating connector 1221, causing the misalignment of the open end of the notch 123 and the open end of the opening 112, forming the receiving perforation. In this way, the rotating member 121 can be urged to rotate by using the actuator 122, and the movement relationship of the open end of the notch 123 can be selectively connected or misaligned with the open end of the opening 112.

Wherein, the rotating connector 1221 and the driving rod 1222 may be provided in the form of a one-piece or assembled combination.

Wherein, the rotating member 121 is next to the rotating notch 124, and a receiving slot is recessed on the periphery corresponding to the driving rod 1222. When the driving rod 1222 is displaced toward the distal end and causes the rotating member 121 to rotate relative to the rotating connector 1221, the driving rod 1222 can be correspondingly displaced into the receiving slot to avoid interfering with the rotation of the rotating member 121.

The driver 13 is located near the proximal end of the receiving space and is used to push the driving rod 1222 for displacement toward the proximal end by a reciprocating motion so that the rotating member 121 can be moved from the starting position to the driving position.

In this embodiment, the driver 13 comprises an operation member 131 and a restoration member 132 used to restore the operation member 131 from the driving position to the starting position. Adjacent to the proximal end, a handle perforation 113 is pierced through the housing 11 and extends along the axial direction. The distal end of the operation member 131 is connected to the proximal end of the driving rod 1222, and the operation member 131 is movable at a position in the axial direction corresponding to the handle perforation 113.

The operation member 131 has a handle structure 133 protruding toward the handle perforation 113 to the outside of the housing 11, so that the displacement distance of the operation member 131 can be limited by the handle perforation 113 and the handle structure 133. The restoration member 132 comprises a resisting ring 1321 fixed and sleeved to the proximal end of the driving rod 1222, a resisting member 1323 protruding from the housing 11 near the distal end of the handle perforation 113, and a spring 1322 mounted on the outer periphery of the driving rod 1222 and abutted against the resisting ring 1321 and the resisting member 1323 at each end thereof.

The spring 1322 is a compression spring, as in FIG. 3, at the starting position, the spring 1322 has no tension, when the operation member 131 is pulled toward the proximal end to the driving position (as in FIG. 4), the driving rod 1222 is displaced toward the forward end together with the resisting ring 1321. At this moment, the spring 1322 receives compression to form a tension, and when the operation member 131 is stopped being pulled, the spring 1322 can drive the operation member 131 back to the starting position based on the elastic restoring force.

The present invention further comprises a limiter 14 for holding the surgical device 10 in the driving position. In this embodiment, the limiter 14 comprises a limiting member 141 and a limiting spring 142. The housing 11 is pierced with a limiting perforation 113 adjacent to the proximal end, and the resisting ring 1321 is recessed with a limiting slot 1324 around the circumference so that the resisting ring 1321 has a smaller outer diameter than the limiting slot 1324.

The limiting spring 142 is a torsion spring whose two ends are connected to the housing 11 and the middle section of the limiting member 141, the two ends of the limiting member 141 form a stop portion 1411 and a release portion 1412 respectively, the limiting member 141 can be rotated in the receiving space according to the torsion spring, and at the same time the stop portion 1411 and the release portion 1412 at two ends may be made to move in opposite directions. According to the relative position of the limiting member 141 during the rotation, the stop portion 1411 is selectively fitted concavely and convexly into the limiting slot 1324 and the release portion 1412 is selectively protruded from the limiting perforation 113.

In the starting position of FIG. 3, the resisting ring 1321 is positioned at the distal end so that the stop portion 1411 is misaligned with the limiting slot 1324, and at that moment the stop portion 1411 is pressed by the larger outer diameter of the resisting ring 1321, causing tension in the torsion spring, and the release portion 1412 at the other end remains in the receiving space and the limiting perforation 114.

When the operation member 131 is pulled and driven to move toward the proximal end so that the limiting slot 1324 corresponds to the stop portion 1411, then the torsion spring drives the limiting member 141 to rotate based on the elastic restoring force so that the stop portion 1411 is displaced toward the limiting slot 1324 and fitted concavely and convexly, and the release portion 1412 at the other end protrudes from the limiting perforation 114 to the outside of the housing 11. The limiter 14 can then fix the surgical device 10 in a suspension state in the driving position.

Then, the release portion 1412 is pressed to rotate the limiting member 141 and cause the stop portion 1411 to release the limiting slot 1324 so that the spring 1322 can drive the operation member 131 back to the starting position based on the elastic restoring force.

Figure 6:
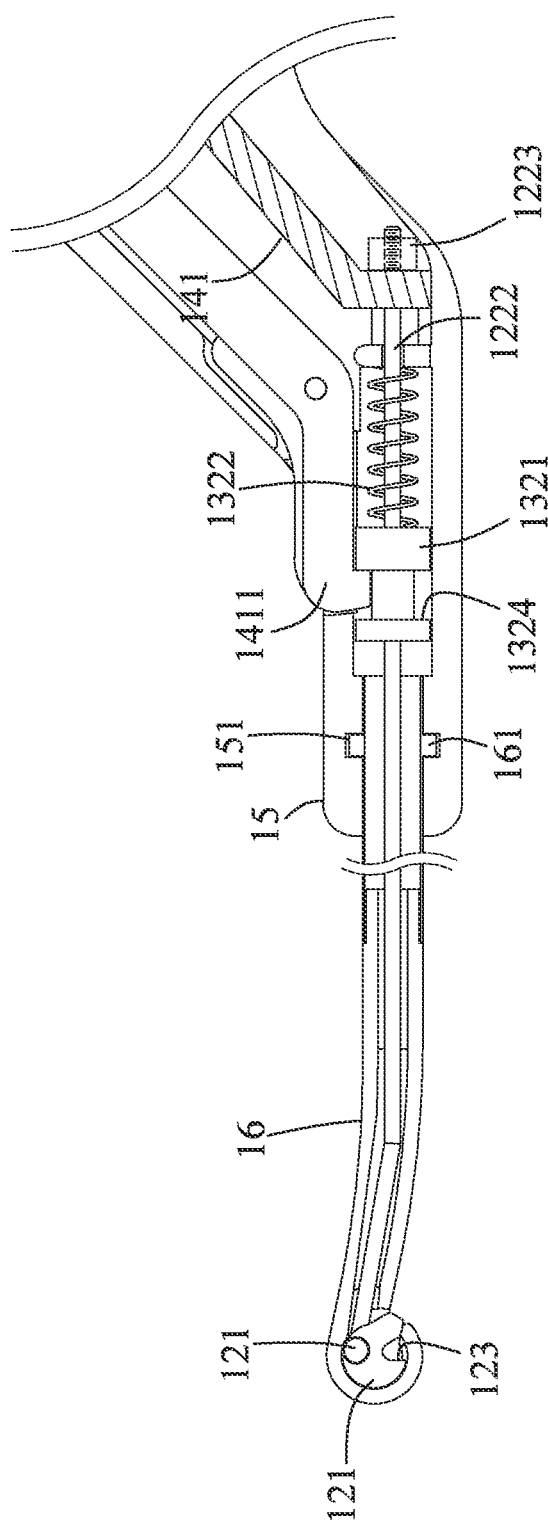
FIG. 6 is a partial enlarged view of the second preferred embodiment of the present invention.

Referring further to FIG. 6, the second embodiment of the present invention differs from the foregoing in that the hook portion 11 is rotatable in the axial direction. In this embodiment, the housing 11 comprises a first housing 15 disposed at the proximal end and a second housing 16 positioned at the distal end corresponding to the hook portion 11 and/or the curved section 118, wherein the distal inner surface of the first housing 15 is annularly recessed with a limiting slot 151, and the proximal surface of the second housing 16 has at least one convex rib 161 protruding from the limiting slot 151, wherein the convex rib may be symmetrically protruded from the surface of the second housing 16 or annularly protruded from the surface of the second housing 16. When the first housing 15 is assembled with the second housing 16, the convex rib 161 is rotatably positioned in the limiting slot 151 so that the second housing 16 can be rotated relative to the first housing 15.

The proximal end of the driving rod 1222 can be rotatably connected to the operation member 131. In this embodiment, the driving rod 1222 crosses the operation member 131 at any position toward the proximal end, and the surface of the proximal end of the driving rod 1222 is screwed with a nut 1223 so that the proximal end of the driving rod 1222 can be rotated on the operation member 131, and the operation member 131 can pull the driving rod 1222 toward the proximal end by pushing the nut 1223.

When the surgical device provided by the present invention is used in a surgical operation, when the open end of the notch 123 is connected to the open end of the opening 112 of the housing 11, a stitch can be grasped through the connected open end and enter the place where the notch 123 and the opening 112 correspond to each other, and further, when the open end of the notch 123 is misaligned with the open end of the opening 112 of the housing 11, the stitch can be retained in the receiving perforation without being detached.

What is claimed is:

1. A surgical device comprising:
    a housing extending in the form of a rod in an axial direction with a receiving space formed therein, a hook portion formed at a distal end of the housing, an opening radially penetrating between a hook end of the hook portion and the housing, and a rotation space formed inside the hook portion together with the opening, the receiving space, the rotation space, and the opening being connected to each other;
    a gripping structure positioned in the housing at the distal end, comprising:
    a rotating member, rotatably disposed in the rotation space, a notch being radially recessed in one periphery of the rotating member, at least a portion of the notch corresponding to at least a portion of the opening; and
    an actuator for rotating the rotating member in a reciprocating motion along the axis so that the open end of the notch is selectively connected to or misaligned with the open end of the opening; and
    a driver for driving the actuator in a reciprocating motion, wherein, when the open end of the notch is misaligned with the open end of the opening, a connected receiving perforation is formed at the location of the notch and the opening corresponding to each other.

2. The surgical device according to claim 1, wherein, the hook portion extends downwardly and arcuately at the distal end of the housing, the rotation space has a circle-like shape, and the rotating member is arranged therein in a circle-like block shape, a diameter of the hook portion is larger than the diameter of the housing adjacent to the hook portion.

3. The surgical device according to claim 1, wherein, the housing has a curved section extending upwardly and arcuately adjacent to the hook portion, and the hook portion is formed along the curved section extending upwardly, and a height difference space is formed under the curved section and the housing, and the end of the hook portion is accommodated in the height difference space.

4. The surgical device according to claim 3, wherein,
    the actuator comprises a rotating connector in the form of a circular block and is connected to one end of a driving rod at any point on its periphery; and
    the rotating member has a rotating notch recessed on the other periphery, the rotating connector is rotatably provided in the rotating notch, and the other end of the driving rod extends towards the proximal end and is driven by the actuator for reciprocating motion, causing the rotating member to rotate relative to the rotating connector.

5. The surgical device according to claim 4, wherein, the rotating member is adjacent to the rotating notch and a receiving slot is recessed on the corresponding periphery of the driving rod, when the driving rod is displaced toward the distal end and cause the rotating member to rotate relative to the rotating connector, the driving rod is entered into the receiving slot.

6. The surgical device according to claim 5, wherein,
    the housing is provided with a handle perforation extending in the direction of the axis adjacent to the proximal end thereof, and a resisting member is protruded adjacent to the distal end of the handle perforation;
    the distal end of the operation member is connected to the proximal end of the driving rod, the operation member has a handle structure protruding toward the handle perforation to the outside of the housing, and the reciprocating motion of the operation member is limited by the handle perforation and the handle structure; and
    the restoration member comprises a resisting ring fixed and sleeved to the proximal end of the driving rod, and a spring mounted on the outer periphery of the driving rod and abutted against the resisting ring and the resisting member at each end thereof, the spring having no tension in the starting position, when the operation member is pulled toward the proximal end and the driving rod is displaced toward the forward end together with the resisting ring to compress the spring.

7. The surgical device according to claim 6, wherein,
the housing is pierced with a limiting perforation adjacent to the proximal end;
the resisting ring is recessed with a limiting slot around the periphery so that the resisting ring is formed with an outer diameter smaller than the limiting slot; and
the limiter comprises a limiting spring whose two ends are connected to the housing and to the middle section of the limiting member, the two ends of the limiting member are a stop portion and a release portion respectively, the limiting member rotating in the receiving space in accordance with the limiting spring, and the stop portion and the release portion being displaced in opposite directions, wherein, in the starting position, the resisting ring being positioned at the distal end so that the stop portion is misaligned with the limiting slot and is pressed by the larger outer diameter of the resisting ring, causing tension in the torsion spring, and the release portion remains in the receiving space and the limiting perforation, when the operation member is moved toward the proximal end so that the limiting slot corresponds to the stop portion, the stop portion is displaced toward the limiting slot, and the release portion protrudes from the limiting perforation to the outside of the housing.

8. The surgical device according to claim 4, the driver is disposed in the housing at the proximal end, comprising:
an operation member for pulling the driving rod towards the proximal end so that the rotating member to move from the starting position to a driving position, the open end of the notch being connected to the open end of the opening in the driving position; and
a restoration member for restoring the operation member from the driving position to the starting position.

9. The surgical device according to claim 8, comprising a limiter for holding the surgical device in the driving position.

10. The surgical device according to claim 8, wherein,
the housing comprises:
a first housing disposed at the proximal end having a limiting slot annularly recessed on the distal inner surface; and
a second housing positioned at the distal end corresponding to the hook portion, having at least one convex rib protruding from the outer surface of the proximal end, wherein
when the first housing is assembled with the second housing, the convex rib is rotatably positioned in the limiting slot so that the second housing is rotatable relative to the first housing; and
the proximal end of the driving rod is rotatably connected with the operation member.

11. The surgical device according to claim 10, wherein, the driving rod crosses the operation member at any position toward the proximal end, and the surface of the proximal end of the driving rod is screwed with a nut, and the operation member pulls the driving rod toward the proximal end by pushing the nut.

12. The surgical device according to claim 1, wherein, the rotating member and the actuator rotate in an axial direction relative to the driver.

* * * * *